United States Patent [19]

Snowden et al.

[11] Patent Number: 5,453,525
[45] Date of Patent: Sep. 26, 1995

[54] CARBOXYLIC ESTERS FOR THE PREPARATION OF A BICYCLIC DECALIN KETONE

[75] Inventors: Roger L. Snowden, Viry, France; Cyril Mahaim, Echichens, Switzerland; Dana P. Simmons, Jamestown, N.C.

[73] Assignee: Firmenich SA, Geneva, Switzerland

[21] Appl. No.: 280,909

[22] Filed: Jul. 27, 1994

Related U.S. Application Data

[62] Division of Ser. No. 94,679, Jul. 20, 1993, Pat. No. 5,386,039.

[30] Foreign Application Priority Data

Jul. 24, 1992 [CH] Switzerland .............................. 2341/92

[51] Int. Cl.$^6$ ................................................. C07C 45/00
[52] U.S. Cl. .................... 554/213; 554/218; 554/220; 554/229; 554/78
[58] Field of Search ............................ 554/213, 229, 554/218, 220, 78

[56] References Cited

U.S. PATENT DOCUMENTS

| | | | |
|---|---|---|---|
| 3,928,246 | 12/1975 | Stadler et al. | 512/19 |
| 3,989,739 | 11/1976 | Eschenmoser et al. | 512/21 |
| 4,007,211 | 2/1977 | Trost et al. | 512/20 |
| 5,334,769 | 8/1994 | Ferrero et al. | 568/435 |

OTHER PUBLICATIONS

S. Harring et al., "Terminator Regulated Mechanistic Divergence in BF$_3$-MeNO$_2$ Promoted Cascade Annulations of Gemetrically Defined Trienoate Derivatives", J. Chem. Commun., pp. 503–505 (1992).

G. Buchi et al., "The Synthesis of Recemic Abrox"; Helvetica Chimica Acta, 72:8, pp. 996–1000 (1989).

Primary Examiner—Arthur C. Prescott
Attorney, Agent, or Firm—Pennie & Edmonds

[57] ABSTRACT

Perhydro-5,5-8a-trimethyl-2-naphthalenone is prepared by acid cyclization of carboxylic esters of formula

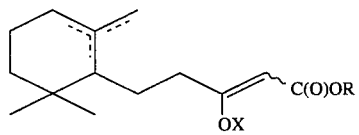

(II)

having a double bond in one of the positions indicated by the dotted lines and wherein symbol R designates a $C_1$–$C_6$ alkyl radical, X stands for a monovalent radical of formula $P(O)(OR^1)_2$ or $C(O)R^2$, $R^1$ represents a $C_1$–$C_6$ alkyl group and $R^2$ is either a linear or branched alkyl group or a substituted or unsubstituted phenyl radical, and wherein the wavy line represents a C—C bond of cis or trans configuration, or of formula

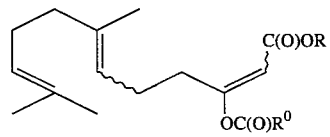

(III)

wherein the wavy lines and symbol R are defined as above, and $R^0$ represents a $C_3$–$C_6$ alkyl radical, preferably branched, followed by basic decarboxylation of the obtained product.

2 Claims, No Drawings

CARBOXYLIC ESTERS FOR THE PREPARATION OF A BICYCLIC DECALIN KETONE

This is a division of application Ser. No. 08/094,679, filed Jul. 20, 1993, now U.S. Pat. No. 5,386,039.

BRIEF SUMMARY OF THE INVENTION

The instant invention relates to a process for the preparation of perhydro-5,5,8a-trimethyl-2-naphthalenone essentially in its isomeric form of formula

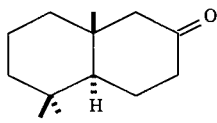

(±) trans which process comprises treating with an acidic cyclization agent a. a carboxylic ester of formula

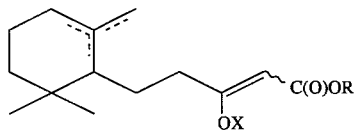

having a double bond in one of the positions indicated by the dotted lines and wherein symbol R designates a $C_1$–$C_6$ alkyl radical, X stands for a monovalent radical of formula $P(O)(OR^1)_2$ or $C(O)R^2$, $R^1$ represents a $C_1$–$C_6$ alkyl group and $R^2$ is either a linear or branched alkyl group or a substituted or unsubstituted phenyl radical, and wherein the wavy line represents a C—C bond of cis or trans configuration, or b. a carboxylic ester of formula

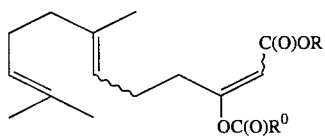

wherein the wavy lines and symbol R are defined as above, and $R^0$ represents a $C_3$–$C_6$ alkyl radical, preferably branched, and decarboxylating then the thus obtained cyclization product by treating it with a base.

This invention provides further carboxylic esters of formula

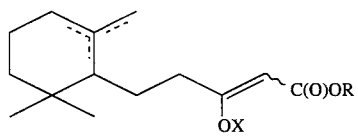

or of formula

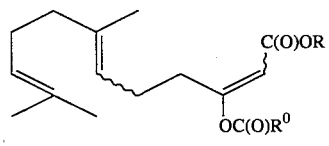

More particularly, it provides the following carboxylic esters: methyl 5-(2,6,6-trimethyl-1-cyclohexen-1-yl)-3-propionoxypent-2-enoate, methyl 5-(2,6,6-trimethyl-1-cyclohexen-1-yl)-3-(2-methylpropionoxy)-pent-2-enoate, methyl 5-(2,6,6-trimethyl-1-cyclohexen-1-yl)-3-(2,2-dimethylpropionoxy)-pent-2-enoate, methyl 5-(2,6,6-trimethyl-1-cyclohexen-1-yl)-3-benzoyl-oxypent-2-enoate, and methyl 7,11-dimethyl-3-(2,2-dimethylpropionoxy)dodeca-2,6,10-trienoate.

BACKGROUND OF THE INVENTION

This invention relates to the field of organic synthesis, more particularly to a process for the preparation of a bicyclic decalin ketone, viz. perhydro-5,5,8a-trimethyl-2-naphthalenone. This ketone is a useful starting material in the synthesis of perhydro-5,5,8a-trimethyl-2-naphthalenyl acetate [Polywood®; trademark of Firmenich SA, Geneva, Switzerland], a fragrance speciality well appreciated for its tenacious and elegant woody note. The ketone itself possesses a strong woody and ambery odor.

Owing to its structure, it may occur under two isomeric forms of formula

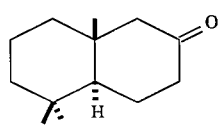

(±) trans and

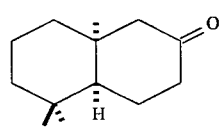

(±) cis their reduction followed by acetylation yielding the desired acetate.

In actual experience it has become apparent that, among the possible isomers, perhydro-5,5,8aα-trimethyl-2α-trans-naphthalenyl acetate is the compound which possesses the most interesting olfactive characters, isomer 2β developing instead a note which, though still woody and ambery, is less rich than the 2α isomer.

French patent 15 93 814 discloses a method for the preparation of ketones (Ia, b) which method is based on the oxidation of a decalin carbinol obtained as follows:

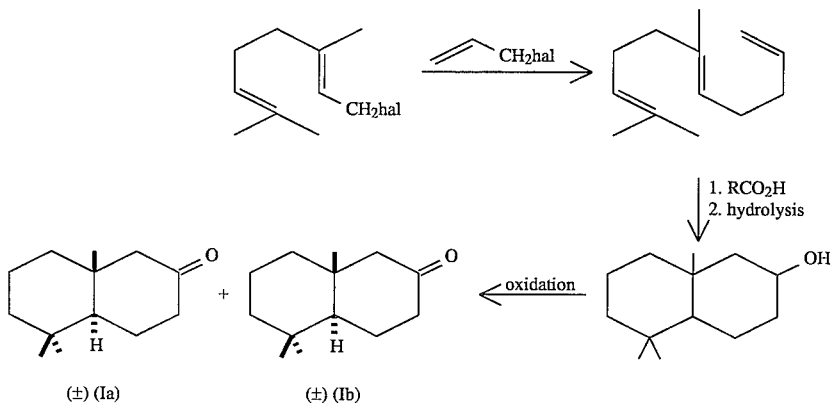

$(\pm)$ (Ia)     $(\pm)$ (Ib)

On account of the above, our efforts were directed to the preparation of perhydro-5,5,8a-trimethyl-2-naphthalenone in its trans isomeric form.

The present invention provides a solution to this problem.

THE INVENTION

One of the objects of the present invention is a process for the preparation of perhydro-5,5,8a-trimethyl-2-naphthalenone essentially in isomeric form (Ia), which process comprises treating with an acidic cyclization agent a. a carboxylic ester of formula

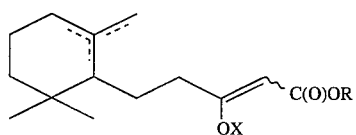

(II)

having a double bond in one of the positions indicated by the dotted lines and wherein symbol R designates a $C_1$–$C_6$ alkyl radical, X stands for a monovalent radical of formula $P(O)(OR^1)_2$ or $C(O)R^2$, $R^1$ represents a $C_1$–$C_6$ alkyl group and $R^2$ is either a linear or branched alkyl group or a substituted or unsubstituted phenyl radical, and wherein the wavy line represents a C—C bond of cis or trans configuration, or b. a carboxylic ester of formula

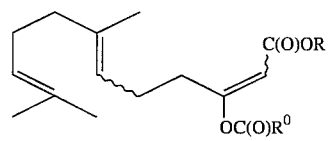

(III)

wherein the wavy lines and symbol R are defined as above, and $R^0$ represents a $C_3$–$C_6$ alkyl radical, preferably branched, and decarboxylating then the thus obtained cyclization product by treating it with a base.

Suitable acidic cyclization agents include mineral or organic protic acids, or Lewis type acids. Typically, one can e.g. use sulfuric, phosphoric, chlorosulfonic, p-toluenesulfonic or formic acid, whereas among the Lewis type acids one could mention $BF_3$. The cyclization can also be effected by means of ion exchange resins.

In practice, it has become apparent that the cyclization reaction occurred with the best rate when the proportion of the acid was of about 2 equivalents for 1 equivalent of the starting ester. The use of higher proportions however does not exert a marked influence on the observed yields.

With regard to the temperature, the cyclization is carried out at about 0°–25° C., preferably at about 5°–10° C.

The subsequent reaction of decarboxylation is effected by analogy with usual techniques by means of known reagents, for instance by means of a base such as an alkali metal hydroxide, e.g. potassium hydroxide, preferably in an alcoholic or an aqueous alcoholic solution, or sodium hydroxide.

As starting materials of formula (II) and (III), there is used an alkyl carboxylic ester chosen for example among the alkyl esters of the following acids: 5-(2,6,6-trimethyl-1-cyclohexen-1-yl)-3-(diethoxyphosphoroxy)-pent-2-enoic, 5-(2,6,6-trimethyl-1-cyclohexen-1-yl)-3-propionoxypent-2-enoic, 5-(2,6,6-trimethyl-1-cyclohexen-1-yl)-3-(2-methylpropionoxy)-pent-2-enoic, 5-(2,6,6-trimethyl-1-cyclohexen-1-yl)-3-(2,2-dimethylpropionoxy)-pent-2-enoic, 5-(2,6,6-trimethyl-1-cyclohexen-1-yl)-3-benzoyloxypent-2-enoic, as well as their isomers 5-(2,6,6-trimethyl-2-cyclohexen-1-ylic)-, and the alkyl ester of 7,11-dimethyl-3-(2,2-dimethylpropionoxy)-dodeca-2,6,10-trienoic acid.

Preferred esters include the methyl, ethyl and propyl ester derivatives, the former being more preferred. As indicated above, these compounds can occur in the cis or trans configuration, owing to the relative position of the carboxylic group with regard to the OX group (compound II) or $OC(O)R^0$ (compound III).

We have observed that the best yields are obtained by the cyclization of the trans esters and that consequently the process is preferably carried out with this type of compounds or with mixtures wherein the contents of the trans isomer is preponderant. Selectivity is equally influenced by the configuration of the starting material, the contents of the trans isomer of perhydro-5,5,8a-trimethyl-2-naphthalenone (compound Ia) is higher when the cylization is carried out on the esters having trans configuration.

Esters (II) are novel compounds and as such they constitute also an object of the invention.

They can be obtained starting from carboalkoxydihydroionones by a simple method by analogy with known technics, as shown by the following reaction scheme.

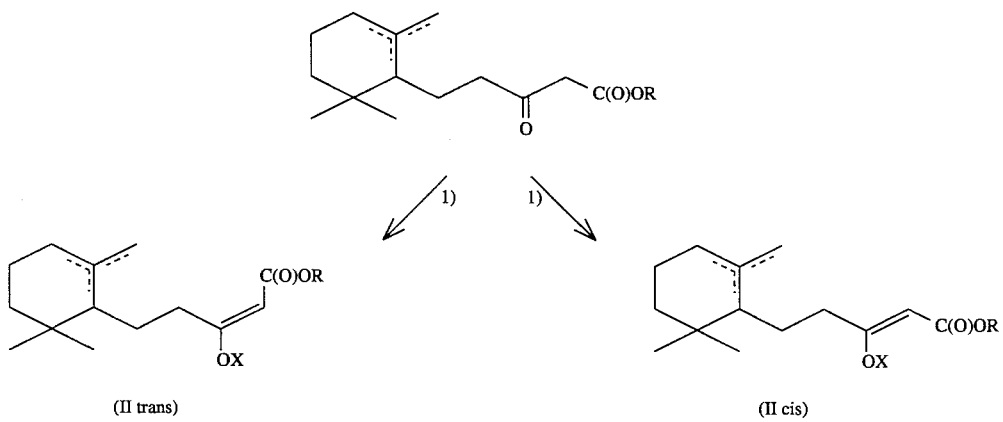

(II trans)        (II cis)

1) see K. Asao et al., Synthesis 1990, 382

By analogy, esters (III) can be obtained starting from carboalkoxygeranyl ketone

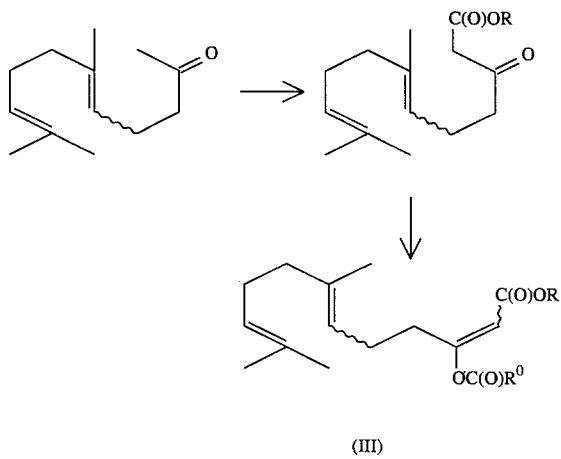

(III)

With the exception of compound (III) wherein $R^0=R=CH_3$ [see Chem. Comm. 1992, 503], compound (III) are new compounds and as such they are also an object of this invention.

The following examples will show the invention in a more detailed manner. The temperatures are indicated in degrees centigrade and the abbreviations have the meaning common in the art.

EXAMPLE 1

Carboxylic esters of formula (II) and (III) have been cyclized according to the following general procedure.

1 g of starting ester in 1 ml of toluene was added dropwise at 2° to a mixture of 2 equivalents of 98% aqueous sulfuric add in 9 ml of toluene.

After 2 h, the reaction mixture was poured in a saturated aqueous solution of sodium bicarbonate and extracted with toluene.

The following step of decarboxylation was carried out on the keto-ester thus obtained by treating it with an alkali metal hydroxide, for example with NaOH.

The following table summarizes the results obtained by the conversion of the esters indicated.

|     | decalin ketone | | yield [%] |
| --- | --- | --- | --- |
|     | Ia | Ib | |
| (a) | 98 | 2 | 81 |
| (b) | 95 | 5 | 72 |
| (c) | 95 | 5 | 49 |
| (d) | 95 | 5 | 61 |
| (e) | 97 | 3 | 79 |
| (f) | 96 | 4 | 70 |

(a) = methyl (E)-5-(2,6,6-trimethyl-1-cyclohexen-1-yl)-3-(diethoxy-phosphoroxy)-pent-2-enoate,
(b) = methyl (Z)-5-(2,6,6-trimethyl-1-cyclohexen-1-yl)-3-(diethoxy-phosphoroxy)-pent-2-enoate,
(c) = methyl 5-(2,6,6-trimethyl-1-cyclohexen-1-yl)-3-propionoxypent-2-enoate,
(d) = methyl 5-(2,6,6-trimethyl-1-cydohexen-1-yl)-3-(2-methylpropionoxy)-pent-2-enoate
(e) = methyl 5-(2,6,6-trimethyl-1-cyclohexen-1-yl)-3-(2,2-dimethyl-propionoxy)-pent-2-enoate
(f) = methyl 5-(2,6,6-trimethyl-1-cyclohexen-1-yl)-3-benzoyloxypent-2-enoate The preparation of the starting esters identified above can be effected as follows:
Preparation of compound (a)

2.3 g (12.9 mM) of diethylchlorophosphate were added under nitrogen at 2° to a stirred solution of 2.5 g (9.4 mM) of methyl 5-(2,6,6-trimethyl-1-cyclohexen-1-yl)- 3-oxopentanoate and 1.3 g (12.8 mM) of triethylamine in 25 ml of N-methyl-pyrrolidone containing 0.04 g (0.3 mM) of 4-(N, N-dimethylamino)-pyridine.

After 1 h at room temperature, the reaction mixture was poured in a saturated aqueous solution of $NH_4Cl$ and extracted with ether. The evaporation of the dried combined organic extracts gave a residue which by column chromatographic separation ($SiO_2$; cyclohexane/AcOEt 1.5:1) and vacuum distillation yielded a yellowish oil (2.4 g, 65%).

B.p. (bulb-to-bulb distillation oven): 200°–220°/6.6 Pa Rf (cyclohexane/AcOEt 1.5:1): 0.36. IR($CHCl_3$): 2933, 1717, 1646, 1437, 1371, 1274, 1162, 1126, 1036. NMR($^1$H): 1.04(s, 6H); 1.39(t, J=7, 6H); 1.43(2H); 1.58(2H); 1.69(s, 3H); 1.93(t, J=6, 2H); 2.27(2H); 2.85(2H); 3.71(s, 3H); 4.22(dq, J=7, 7, 4H); 5.86(broad s, 1H) δ ppm. NMR($^{13}$C): 166.7(8)(s); 135.8(s); 128.7(s); 104.6(d); 64.8(9)(t); 51.3(q); 39.9(t); 35.1(s); 32.9(t); 32.6(t); 28.5(q); 25.8(t); 19.7(q); 19.5(t); 16.1(q) δ ppm. MS: 388(5, M$^+$), 252(41), 220(69), 192(29), 155(100), 127(37), 99(65).
Preparation of compound (b)

A solution of 2.5 g (9.4 mM) of methyl 5-(2,6,6-trimethyl-1-cyclohexen-1-yl)-3-oxopentanoate in 10 ml of tetrahydrofurane (THF) was added dropwise at room temperature to a stirred mixture of NaH (80% in mineral oil; 0.3 g; 0.01M) in 25 ml of THF.

After 1 h at room temperature, 2.3 g (12.9 mM) of diethylchlorophosphate were added dropwise to the mixture.

After 50 min the mixture was cooled and poured carefully into a cold saturated aqueous solution of $NH_4Cl$ and extracted with ether.

The usual work up gave a residue which by column chromatography ($SiO_2$; cyclohexane/AcOEt 2:1) followed by distillation yielded 3.1 g (yield 84%) of a colorless oil.

B.p. (bulb-to-bulb distillation oven): 200°–220°/6.6 Pa $R_f$ (cyclohexane/AcOEt 1.5:1): 0.29. IR($CHCl_3$): 2934, 1725, 1664, 1436, 1274, 1201, 1149, 1032. NMR($^1H$): 1.00(s, 6H); 1.37(t, J=7, 6H); 1.41(2H); 1.57(2H); 1.61(s, 3H); 1.91(broad t, J=7, 2H); 2.26(2H); 2.48(2H); 3.71(s, 3H); 4.27(dq, J=7, 7, 4H); 5.41(s, 1H) δ ppm. NMR($^{13}C$): 164.4(s); 162.5(s); 162.4(s); 135.5(s); 128.8(s); 104.5(6)(t); 64.7(8)(t); 51.1(q); 39.9(t); 35.7(t); 35.0(s); 32.8(t); 28.5(2q); 28.1(t); 19.8(q); 19.5(t); 16.1(2q) δ ppm. MS: 388(1, M$^+$), 252(100), 220(68), 192(28), 155(53), 99(48).

Preparation of compound (c)

1.0 g (10.8 mM) of propionyl chloride was added at room temperature dropwise within 15 min to a stirred solution of 2.5 g (9.4 mM) of methyl 5-(2,6,6-trimethyl-1-cyclohexen-1-yl)-3-oxopentanoate and 1.1 g (10.8 mM) of triethylamine in 30 ml of toluene.

After 2 h at room temperature, the mixture was poured into a saturated aqueous solution of $NH_4Cl$ and extracted with toluene. The usual work up, followed by vacuum distillation gave the desired product under the form of an isomeric mixture trans/cis 1:1 (colorless viscous oil; 1.6 g; yield 55%).

B.p.: 125°–140°/33 Pa IR($CHCl_3$): 2940, 1760, 1718, 1436, 1360, 1230, 1138.

The trans isomer showed the following characteristics: $R_f$ (cyclohexane/AcOEt 9:1): 0,45. NMR($^1H$): 1.02(s, 6H); 1.22(t, J=7, 3H); 1.42(2H); 1.56(2H); 1.65(s, 3H); 1.91(2H); 2.19(2H); 2.49(q, J=7, 2H); 2.86(2H); 3.72(s, 3H); 5.67(s, 1H) δ ppm. NMR($^{13}C$): 171.4(s); 167.1(s); 166.2(s); 136.0(s); 128.6(s); 109.2(d); 51.3(q); 39.9(t); 35.1(s); 32.8(t); 32.0(t); 28.5(2q); 27.7(t); 25.7(t); 19.7(q); 19.5(t); 8.9(q) δ ppm. MS: 308(0, M$^+$), 219(8), 137(90), 95(48), 81(35), 57(100).

The cis isomer was characterized by the following parameters: $R_f$ (cyclohexane/AcOEt 9:1): 0,36. NMR($^1H$): 0.98(s, 6H); 1.24(t, J=7, 3H); 1.42(2H); 1.56(2H); 1.59(s, 3H); 1.91(2H); 2.20(2H); 2.32(2H); 2.57(q, J=7, 2H); 3.68(s, 3H); 5.63(s, 1H) δ ppm. NMR($^{13}C$): 171.7(s); 164.5(s); 164.0(s); 135.6(s); 128.5(s); 106.5(d); 51.2(q); 39.8(t); 36.1(s); 35.0(s); 32.9(t); 28.5(2q); 27.9(t); 25.2(t); 19.6(q); 19.5(t); 8.0(q) δ ppm. MS: 308(0, M$^+$), 219(12), 137(49), 95(41), 81(31), 57(100).

Compound (d) was prepared according to the same procedure as that described hereinabove by using 2-methylpropionyl chloride as reagent. Compound (d) was thus obtained in the form of a trans/ds (3.3:1) isomeric mixture; 2.0 g; yield 66%.

B.p.: 130°–136°/40 Pa IR($CHCl_3$): 2936, 1752, 1718, 1662, 1437, 1361, 1232, 1099.

Isomer trans: $R_f$ (cyclohexane/AcOEt 9:1): 0.48. NMR($^1H$): 1.02(s, 6H); 1.26(d, J=7, 6H); 1.42(2H); 1.56(2H); 1.65(s, 3H); 1.91(2H); 2.19(2H); 2.69(m, 1H); 2.86(2H); 3.72(s, 3H); 5.65(s, 1H) δ ppm. NMR($^{13}C$): 174.3(s); 167.2(s); 166.2(s); 135.9(s); 128.6(s); 109.1(d); 51.3(q); 40.0(t); 35.1(s); 34.4(d); 32.9(t); 31.9(t); 28.5(2q); 25.7(t); 19.7(q); 19.5(t); 16.9(2q) δ ppm. MS: 322(4, M$^+$), 234(9), 219(7), 137(81), 71(100).

Isomer cis: $R_f$ (cyclohexane/AcOEt 9:1): 0.39. NMR($^1H$): 0.98(s, 6H); 1.29(d, J=7, 6H); 1.42(2H); 1.56(2H); 1.58(s, 3H); 1.91(2H); 2.19(2H); 2.29(2H); 2.78(m, 1H); 3.67(s, 3H); 5.62(s, 1H) δ ppm. NMR($^{13}C$): 174.3(s); 167.2(s); 164.5(s); 135.6(s); 128.6(s); 106.8(d); 51.1(q); 39.8(t); 36.0(t); 35.0(s); 34.2(d); 32.8(t); 28.5(2q); 25.3(t); 19.7(q); 19.5(t); 16.9(2q) δ ppm. MS: 322(0, M$^+$), 234(7), 219(11), 137(42), 71(100).

Compound (e) was prepared according to the same procedure as that described hereinabove by using 2,2-dimethylpropionyl chloride as reagent. Compound (e) was obtained in the form of a trans/cis (>9:1) isomeric mixture; 2.6 g; yield 82%.

B.p.: 140°14 145°/40 Pa IR($CHCl_3$): 2934, 1745, 1717, 1660, 1436, 1361, 1216, 1098.

Isomer trans: $R_f$ (cyclohexane/AcOEt 9:1): 0.52. NMR($^1H$): 1.02(s, 6H); 1.30(s, 9H); 1.42(2H); 1.57(2H); 1.66(s, 3H); 1.92(2H); 2.20(2H); 2.87(2H); 3.72(s, 3H); 5.62(s, 1H) δ ppm. NMR($^{13}C$): 175.8(s); 167.5(s); 166.2(s); 135.9(s); 128.6(s); 109.0(d); 51.3(q); 40.0(t); 39.3(s); 35.1(s); 32.9(t); 31.9(t); 28.5(2q); 27.1(3q); 25.7(t); 19.7(q); 19.5(t) δ ppm. MS: 336(0, M$^+$), 137(31), 95(12), 85(19), 57(100).

Isomer cis: $R_f$ (cyclohexane/AcOEt 9:1): 0.44. NMR($^1H$): 0.98(s, 6H); 3.67(s, 3H) δ ppm.

Preparation of compound (f)

1.5 ml (12.9 mM) of benzoyl chloride were added dropwise at 2° in a nitrogen atmosphere to a stirred solution of 2.5 g (9.4 mM) of methyl 5-(2,6,6-trimethyl-1-cyclohexen-1-yl)-3-oxopentanoate, 1.3 g (12.8 mM) of triethylamine in 30 ml of toluene containing 0.04 g (0.3 mM) of 4-(N,N-dimethylamino)pyridine.

After 2.5 h at room temperature, the reaction mixture was poured into a saturated aqueous solution of $NH_4Cl$ and extracted with ether.

The usual work up followed by distillation gave desired ester (f) in the form of a trans/cis (53:47) isomeric mixture: 3.3 g; yield 93%.

A chromatographic separation on column allowed to obtain compound (f) in the pure trans and cis isomeric form.

Isomer trans: B.p. (bulb-to-bulb distillation oven): 200°–220°/8 Pa $R_f$ (cyclohexane/AcOEt 9:1): 0.43. IR($CHCl_3$): 2932, 1735, 1661, 1437, 1361, 1261, 1203, 1159, 1104, 1067, 1028. NMR($^1H$): 1.00(s, 6H); 1.40(2H); 1.55(2H); 1.62(s, 3H); 1.89(broad t, J=7, 2H); 2.29(m, 2H); 3.01(m, 2H); 3.75(s, 3H); 5.83(s, 1H); 7.50(t, J=8, 2H); 7.63(broad t, J=7, 1H); 8.10(broad d, J=7.5, 2H) δ ppm. NMR($^{13}C$): 167.2(s); 166.2(s); 164.0(s); 135.9(s); 133.8(d); 130.1(2d); 129.2(s); 128.7(2d); 128.6(s); 109.5(d); 51.4(q); 39.9(t); 35.0(s); 32.9(t); 32.0(t); 28.5(2q); 25.7(t); 19.6(q); 19.5(t) δ ppm. MS: 356(0, M$^+$), 137(22), 105(100), 77(16).

Isomer cis: B.p. (bulb-to-bulb distillation oven): 200°–220°/8 Pa $R_f$ (cyclohexane/AcOEt 9:1): 0.34. IR($CHCl_3$): 2933, 1729, 1667, 1437, 1270, 1199, 1175, 1139, 1083, 1066, 1026. NMR($^1H$): 0.99(s, 6H); 1.41(2H); 1.56(2H); 1.64(s, 3H); 1.90(broad t, J=7, 2H); 2.30(m, 2H); 2.47(m, 2H); 3.61(s, 3H); 5.74(s, 1H); 7.48(t, J=8, 2H); 7.61(t, J=7, 1H); 8.14(broad d, J=7.5, 2H) δ ppm. NMR($^{13}C$): 164.4(s); 163.9(s); 163.8(s); 135.5(s); 133.5(d); 130.2(2d); 129.5(s); 128.7(s); 128.6(2d); 107.0(d); 51.3(q); 39.8(t); 36.1(s); 35.0(s); 32.8(t); 28.5(2q); 25.2(t); 19.8(q); 19.4(t) δ ppm. MS: 356(0, M$^+$), 241(3), 137(9), 105(100), 77(19).

Methyl 5-(2,6,6-trimethyl-1-cyclohexen-1-yl)-3-oxopentanoate, used as starting material in the process above can be obtained according to the method described by G. Büchi and H. Wüest, Helv. Chim. Acta 72, 996 (1989).

EXAMPLE 2

1060 g of 98% aqueous sulfuric acid and 2l of toluene were poured into a three necked reaction vessel equipped with a mechanical stirrer, a thermometer, a condenser and a dropping funnel. The mixture was cooled to 3°–4°, thereupon 1060 g (3.14M) of methyl 7,11-dimethyl-3-(2,2,-dimethylpropionoxy)-dodeca- 2,6,10-trienoate where added dropwise thereto. During the addition the temperature was carefully kept below 15°, then the mixture was kept under stirring for 1.5 h at 5°–10°. 1 kg of crushed ice was then slowly added to the reaction mixture while the temperature was maintained below 20°.

After decantation, the mixture was washed with a saturated aqueous solution of sodium bicarbonate and extracted with toluene.

The following step of decarboxylation was carried out by treatment with a sodium hydroxide aqueous solution.

For a quantity of 1060 g (3.13M) of perhydro-5,5,8a-trimethyl-3-carbomethoxy-2-naphthalenone there were used 2720 g of a 30% aqueous solution of NaOH.

423.5 g (1.66M) of perhydro-5,5,8a-trimethyl-2-naphthalenone were thus obtained, the trans isomeric contents of which was 76%. Other acidic cyclization reactions of methyl 7,11-dimethyl-3-(2,2-dimethylpropionoxy)-dodeca-2,6,10-trienoate were carried out by replacing sulfuric acid by formic acid, phosphoric acid and $BF_3$ under the form of trifluoroboroetherate.

The starting methyl ester was prepared as described hereinafter starting from a trans enriched fraction of geranylacetone.

24 g (0.55M) of sodium hydride (55% dispersion in mineral oil) were added at 20° under nitrogen to a solution of 135 g (1.5M) of dimethylcarbonate in 500 ml of a mixture of toluene/N-methylpyrrolidone (9:1). The obtained mixture was heated to reflux (bath temperature 100°) then, during 1 h, there was added a solution of 0.5M of geranylacetone in 135 g (1.5M) of dimethylcarbonate, where upon the resulting reaction mixture was kept refluxing during 10 min. It was finally poured into a 10% aqueous solution of $NH_4Cl$ saturated with NaCl. An ether extraction, followed by the usual work up of the combined organic extracts and fractional distillation gave methyl 3-oxo-7,11-dimethyl-dodeca-6,10-dienoate.

b. A mixture of 796 g of the obtained keto-ester in 200 ml of 80–100 petrol ether (3.16M) and 349.5 g (3.46M) of triethylamine was charged in a three necked vessel equipped with a thermometer, a dropping funnel and a mechanical stirrer. To the resulting mixture heated to 70°, there were added within 2 h under stirring 388 g (3.22M) of pivaloyl chloride.

After cooling, the mixture was washed with two fractions of 900 ml each of water and the organic phase was concentrated to give 1060 g of methyl 7,11-dimethyl-3-(2,2-dimethyl-propionoxy)-dodeca-2,6,10-trienoate, the analytical characters of which were the following:

NMR($^1$H, 360 MHz, $CDCl_3$): 1.27 and 1.28(2s, 9H); 1.60 and 1.68(2 broad s, 9H); 1.94–2.08(m, 4H); 2.21(q, J=7, 2H); 2.82 and 2.84(2 tr, J=7, 2H); 3.71(s, 3H); 5.08 and 5.15(2 broad t, J=7, 2H) 5.65(s, 1H) δ ppm. NMR($^{13}$C, 90.5 MHz, $CDCl_3$): 15.9(q); 17.7(2q); 23.4(q); 25.3(t); 25.7(2q); 26.6(t)1 26.7(t); 27.0(6q); 31.2(t); 31.5(t); 31.9(t); 39.3(2s); 39.7(2t); 51.3(2q); 109.5(2d); 122.5(2d); 123.4(d); 124.3(d); 131.4(s); 131.6(s); 136.6(2s); 166.2(s); 166.3(s); 167.4(2s); 175.8(2s) δ ppm. MS: 336(0, M$^+$), 57(100), 69(36), 85(17), 41(17), 81(10), 109(7), 123(6), 67(6), 151(5), 101(5), 136(4), 95(4).

What we claim is:

1. A carboxylic ester of formula

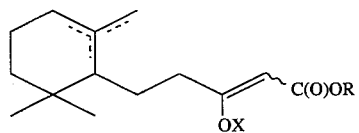

(II)

having a double bond in one of the positions indicated by the dotted lines and wherein symbol R designates a $C_1$–$C_6$ alkyl radical, X stands for a monovalent radical of formula $P(O)(OR^1)_2$ or $C(O)R^2$, $R^1$ represents a $C_1$–$C_6$ alkyl group and $R^2$ is either a linear or branched alkyl group or a substituted or unsubstituted phenyl radical, and wherein the wavy line represents a C—C bond of cis or trans configuration, or of formula

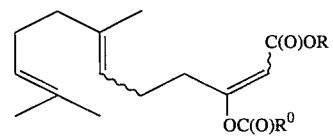

(III)

wherein the wavy lines and symbol R are defined as above, and $R^0$ represents a $C_3$–$C_6$ alkyl radical, preferably branched.

2. A carboxylic ester according to claim 1 chosen among the group consisting of:

methyl 5-(2,6,6-trimethyl-1-cyclohexen-1-yl)-3-(diethoxyphosphoroxy)pent-2-enoate, methyl 5-(2,6,6-trimethyl-1-cyclohexen-1-yl)-3-propionoxypent-2-enoate, methyl 5-(2,6,6-trimethyl-1-cyclohexen-1-yl)-3-(2-methylpropionoxy)pent-2-enoate, methyl 5-(2,6,6-trimethyl-1-cyclohexen-1-yl)-3-(2,2-dimethylpropionoxy)-pent-2-enoate, methyl 5-(2,6,6-trimethyl-1-cyclohexen-1-yl)-3-benzoyloxypent-2-enoate, and methyl 7,11-dimethyl-3-(2,2-dimethylpropionoxy)dodeca-2,6,10-trienoate.

* * * * *